United States Patent
Fenech et al.

(10) Patent No.: US 11,419,689 B2
(45) Date of Patent: Aug. 23, 2022

(54) GUIDE APPARATUS FOR DELIVERY OF A FLEXIBLE INSTRUMENT AND METHODS OF USE

(71) Applicant: INTUITIVE SURGICAL OPERATIONS, INC., Sunnyvale, CA (US)

(72) Inventors: Carolyn M. Fenech, San Jose, CA (US); Eleadin Castaneda, San Jose, CA (US); Benjamin E. Goodman, Menlo Park, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 513 days.

(21) Appl. No.: 16/446,015

(22) Filed: Jun. 19, 2019

(65) Prior Publication Data

US 2020/0069384 A1 Mar. 5, 2020

Related U.S. Application Data

(63) Continuation of application No. 15/329,916, filed as application No. PCT/US2015/040415 on Jul. 14, 2015, now Pat. No. 10,413,372.

(Continued)

(51) Int. Cl.
*A61M 31/00* (2006.01)
*A61M 37/00* (2006.01)
(Continued)

(52) U.S. Cl.
CPC .............. *A61B 34/35* (2016.02); *A61B 34/20* (2016.02); *A61B 34/30* (2016.02); *A61B 34/37* (2016.02);
(Continued)

(58) Field of Classification Search
CPC ...... A61B 2034/2061; A61B 2034/301; A61B 2034/715; A61B 34/20; A61B 34/30;
(Continued)

(56) References Cited

U.S. PATENT DOCUMENTS 2,130,993 A 9/1938 Dubiller
3,213,573 A 10/1965 Bohr et al.
(Continued)

FOREIGN PATENT DOCUMENTS

CN 101820824 A 9/2010
EP 2354006 A1 8/2011
(Continued)

OTHER PUBLICATIONS

Extended European Search Report for Application No. EP15826509, dated Mar. 27, 2018, 8 pages.
(Continued)

*Primary Examiner* — Rebecca E Eisenberg
(74) *Attorney, Agent, or Firm* — Haynes and Boone, LLP

(57) ABSTRACT

A guiding apparatus comprises a plurality of support members. Each of the plurality of support members has a curved profile to resist bending in at least one direction. The guiding apparatus also comprises a retraction system coupled to the plurality of support members. The plurality of support members has an extended configuration in which the plurality of support members is positioned in an arrangement to form a channel sized to receive an instrument. The plurality of support members has a retracted configuration in which each of the plurality of support members is retracted within the retraction system as the instrument is advanced along a longitudinal axis.

20 Claims, 10 Drawing Sheets

Related U.S. Application Data

(60) Provisional application No. 62/029,917, filed on Jul. 28, 2014.

(51) Int. Cl.
*A61B 34/35* (2016.01)
*A61B 90/50* (2016.01)
*A61B 34/30* (2016.01)
*A61B 34/20* (2016.01)
*A61B 34/37* (2016.01)
*A61B 34/00* (2016.01)

(52) U.S. Cl.
CPC .............. *A61B 34/74* (2016.02); *A61B 34/76* (2016.02); *A61B 90/50* (2016.02); *A61B 2034/2061* (2016.02); *A61B 2034/301* (2016.02); *A61B 2034/306* (2016.02); *A61B 2034/715* (2016.02); *A61B 2034/741* (2016.02); *A61B 2034/742* (2016.02)

(58) Field of Classification Search
CPC ......... A61B 34/35; A61B 34/37; A61B 34/76; A61B 90/50
See application file for complete search history.

(56) References Cited

U.S. PATENT DOCUMENTS

| | | | |
|---|---|---|---|
| 6,331,181 | B1 | 12/2001 | Tierney et al. |
| 6,491,701 | B2 | 12/2002 | Tierney et al. |
| 6,875,170 | B2 | 4/2005 | Francois et al. |
| 8,900,131 | B2 | 12/2014 | Chopra et al. |
| 9,452,276 | B2 | 9/2016 | Duindam et al. |
| 2004/0254566 | A1 | 12/2004 | Plicchi et al. |
| 2007/0008967 | A1 | 1/2007 | Bressler et al. |
| 2008/0064921 | A1 | 3/2008 | Larkin et al. |
| 2010/0204646 | A1 | 8/2010 | Plicchi et al. |
| 2011/0282351 | A1 | 11/2011 | Cooper et al. |
| 2012/0071752 | A1 | 3/2012 | Sewell et al. |
| 2014/0118515 | A1 | 5/2014 | Lee |
| 2014/0171919 | A1 | 6/2014 | Blacker |
| 2014/0180308 | A1 | 6/2014 | Von Grünberg |
| 2017/0265953 | A1 | 9/2017 | Fenech et al. |
| 2018/0125593 | A1 | 5/2018 | Sinibaldi et al. |

FOREIGN PATENT DOCUMENTS

| | | |
|---|---|---|
| WO | WO-2007008967 A2 | 1/2007 |
| WO | WO-2011037718 A1 | 3/2011 |

OTHER PUBLICATIONS

International Search Report and Written Opinion for Application No. PCT/US15/040415, dated Oct. 16, 2015, 13 pages.
International Preliminary Report on Patentability for Application No. PCT/US2015/040415, dated Feb. 9, 2017, 8 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

GUIDE APPARATUS FOR DELIVERY OF A FLEXIBLE INSTRUMENT AND METHODS OF USE

CROSS-REFERENCE TO RELATED APPLICATIONS

This patent application is a continuation application of U.S. application Ser. No. 15/329,916, filed Jan. 27, 2017, which is the U.S. national phase of International Application No. PCT/US2015/040415, filed on Jul. 14, 2015, which designated the U.S. and claims priority to and the benefit of the filing date of U.S. Provisional Patent Application No. 62/029,917, entitled "GUIDE APPARATUS FOR DELIVERY OF FLEXIBLE INSTRUMENT AND METHOD OF USE," filed Jul. 28, 2014, all of which are incorporated by reference herein in their entireties.

FIELD

The present disclosure is directed to systems and methods for navigating a patient anatomy to conduct a minimally invasive procedure, and more particularly to apparatus and methods for guiding and supporting delivery of a flexible interventional instrument into a patient anatomy.

BACKGROUND

Minimally invasive medical techniques are intended to reduce the amount of tissue that is damaged during interventional procedures, thereby reducing patient recovery time, discomfort, and deleterious side effects. Such minimally invasive techniques may be performed through natural orifices in a patient anatomy or through one or more surgical incisions. Through these natural orifices or incisions clinicians may insert interventional instruments (including surgical, diagnostic, therapeutic, or biopsy instruments) to reach a target tissue location. To reach the target tissue location, a minimally invasive interventional instrument may navigate natural or surgically created passageways in anatomical systems such as the lungs, the colon, the intestines, the kidneys, the heart, the circulatory system, or the like. Teleoperation interventional systems may be used to insert the interventional instruments into the patient anatomy. In existing systems, the length of the interventional instrument extending between the patient and a teleoperational manipulator is unsupported which may cause the instrument to bend and buckle as it is inserted into the patient anatomy. Deformation of the instrument may damage internal components such as optical fiber shape sensors or endoscopic equipment. Improved systems and methods are needed for guiding and supporting interventional instruments as they are inserted into a patient anatomy to prevent instrument deformation.

SUMMARY

The embodiments of the invention are summarized by the claims that follow the description.

In one embodiment, a guiding apparatus comprises a plurality of collapsible support members and a plurality of retraction assemblies. Each of the plurality of retraction assemblies is coupled to a respective one of the plurality of collapsible support members. The plurality of collapsible support members have an extended configuration in which the plurality of support members are arranged to form a channel extending along a longitudinal axis. The channel is sized to receive an elongated instrument. The plurality of support members have a collapsed configuration in which each of the plurality of support members is retracted within the respective coupled retraction assembly as the elongated instrument is advanced along the longitudinal axis.

In another embodiment, a system comprises an elongated instrument configured to couple with a teleoperational manipulator assembly for advancement along a longitudinal axis. The system also includes a support assembly including a retractable channel formed from a plurality of support members, the channel sized to receive the elongated instrument and a retraction system coupled to the plurality of support members. The retraction system is operable to retract the plurality of support members as the elongated instrument is advanced along the longitudinal axis.

In another embodiment, a method of supporting an elongated medical instrument comprises advancing the elongated medical instrument along a longitudinal axis through a retractable support channel and retracting the retractable support channel as the elongated medical instrument is advanced. The retractable support channel including a plurality of support members retractable in unison. The method also includes retracting each of the plurality of support members into a retraction housing.

Additional aspects, features, and advantages of the present disclosure will become apparent from the following detailed description.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

DETAILED DESCRIPTION

In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention. And, to avoid needless descriptive repetition, one or more components or actions described in accordance with one illustrative embodiment can be used or omitted as applicable from other illustrative embodiments.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y. Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Figure 1:
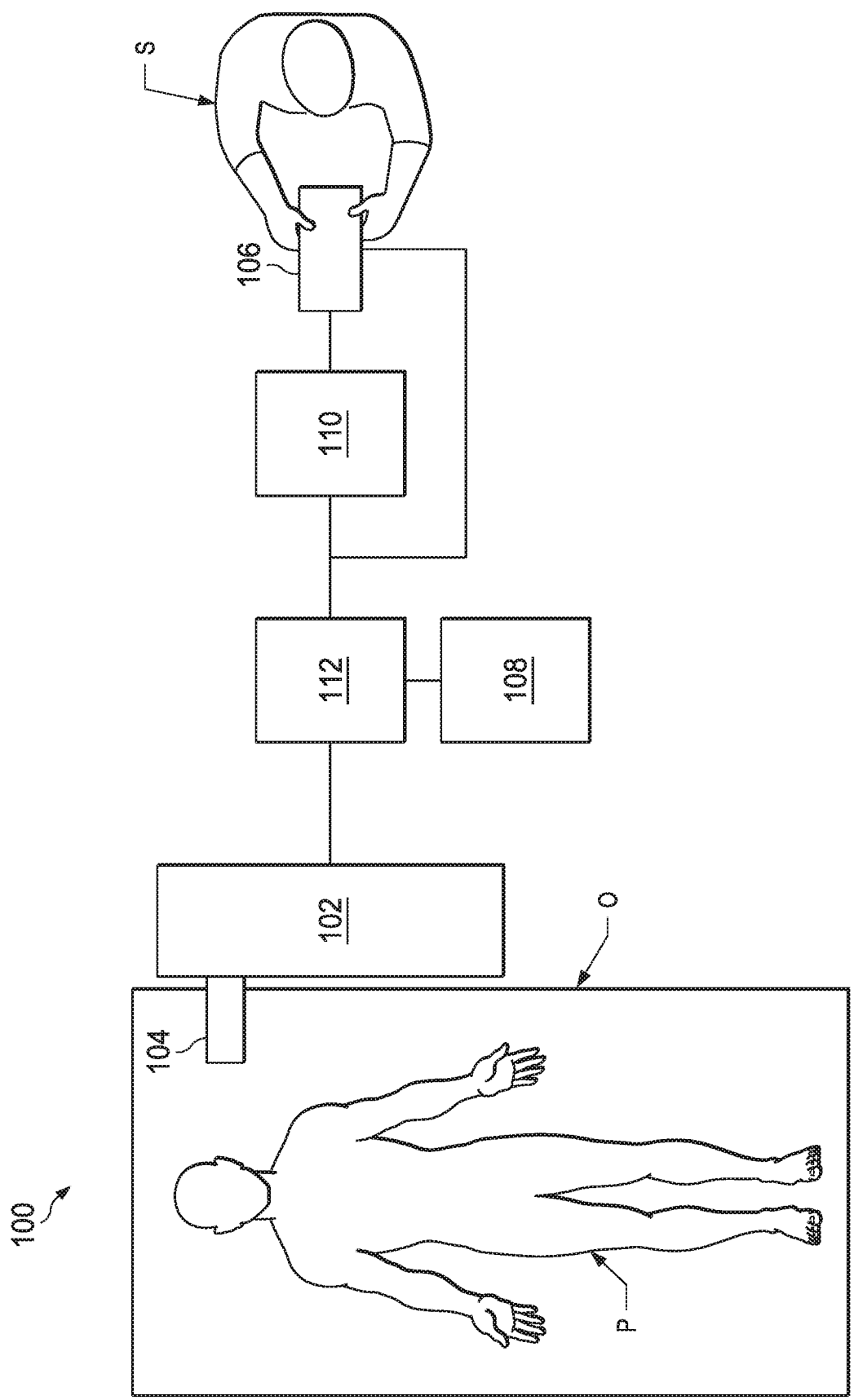
FIG. 1 is a teleoperational interventional system, in accordance with an embodiment of the present disclosure.

Referring to FIG. 1 of the drawings, a teleoperated interventional system for use in, for example, surgical, diagnostic, therapeutic, or biopsy procedures, is generally indicated by the reference numeral 100. As shown in FIG. 1, the teleoperated system 100 generally includes an interventional manipulator assembly 102 for operating an interventional instrument 104 in performing various procedures on the patient P. The assembly 102 is mounted to or near an operating table 0. An operator input system 106 allows the clinician or surgeon S to view the interventional site and to control the slave manipulator assembly 102.

The operator input system 106 may be located at a surgeon's console which is usually located in the same room as operating table 0. However, it should be understood that the surgeon S can be located in a different room or a completely different building from the patient P. The operator input system 106 generally includes one or more control devices for controlling the manipulator assemblies 102. The control devices may include any number of a variety of input devices, such as joysticks, trackballs, data gloves, trigger-guns, hand-operated controllers, voice recognition devices, body motion or presence sensors, or the like. In some embodiments, the control devices will be provided with the same degrees of freedom as the associated interventional instruments 104 to provide the surgeon with telepresence, or the perception that the control devices are integral with the instruments 104 so that the surgeon has a strong sense of directly controlling instruments 104. In other embodiments, the control devices may have more or fewer degrees of freedom than the associated interventional instruments 104 and still provide the surgeon with telepresence. In some embodiments, the control devices are manual input devices which move with six degrees of freedom, and which may also include an actuatable handle for actuating instruments (for example, for closing grasping jaws, applying an electrical potential to an electrode, delivering a medicinal treatment, or the like).

The teleoperational assembly 102 supports the medical instrument system 104 and may include a kinematic structure of one or more non-servo controlled links (e.g., one or more links that may be manually positioned and locked in place, generally referred to as a set-up structure) and a teleoperational manipulator. The teleoperational assembly 102 includes plurality of actuators or motors that drive inputs on the medical instrument system 104 in response to commands from the control system (e.g., a control system 112). The motors include drive systems that when coupled to the medical instrument system 104 may advance the medical instrument into a naturally or surgically created anatomical orifice. Other motorized drive systems may move the distal end of the medical instrument in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the motors can be used to actuate an articulable end effector of the instrument for grasping tissue in the jaws of a biopsy device or the like.

The teleoperational medical system 100 also includes a sensor system 108 with one or more sub-systems for receiving information about the instruments of the teleoperational assembly. Such sub-systems may include a position sensor system (e.g., an electromagnetic (EM) sensor system); a shape sensor system for determining the position, orientation, speed, velocity, pose, and/or shape of the catheter tip and/or of one or more segments along a flexible body of instrument system 104; and/or a visualization system for capturing images from the distal end of the catheter system.

The visualization system (e.g., visualization system 231 of FIG. 2) may include a viewing scope assembly (described in greater detail below) such that a concurrent or real-time image of the surgical site is provided to clinician or surgeon S. The concurrent image may be, for example, a two or three dimensional image captured by an endoscope positioned within the surgical site. In this embodiment, the visualization system includes endoscopic components that may be integrally or removably coupled to the medical instrument 104. However in alternative embodiments, a separate endoscope, attached to a separate manipulator assembly may be used with the medical instrument to image the surgical site. The visualization system may be implemented as hardware, firmware, software or a combination thereof which interact with or are otherwise executed by one or more computer processors, which may include the processors of a control system 112 (described below).

The teleoperational medical system 100 also includes a display system 110 for displaying an image or representation of the surgical site and medical instrument system(s) 104 generated by sub-systems of the sensor system 108. The display 110 and the operator input system 106 may be oriented so the operator can control the medical instrument system 104 and the operator input system 106 with the perception of telepresence.

The display system 110 may also display an image of the surgical site and medical instruments captured by the visualization system. The display 110 and the control devices may be oriented such that the relative positions of the imaging device in the scope assembly and the medical instruments are similar to the relative positions of the surgeon's eyes and hands so the operator can manipulate the medical instrument 104 and the hand control as if viewing the workspace in substantially true presence. By true presence, it is meant that the presentation of an image is a true perspective image simulating the viewpoint of an operator that is physically manipulating the instrument 104.

Alternatively or additionally, the display 110 may present images of the surgical site recorded and/or modeled preoperatively using data from imaging technology such as, computed tomography (CT), magnetic resonance imaging (MRI), fluoroscopy, thermography, ultrasound, optical coherence tomography (OCT), thermal imaging, impedance imaging, laser imaging, or nanotube X-ray imaging. The presented preoperative images may include two-dimensional, three-dimensional, or four-dimensional images. The presented preoperative or intra-operative images may include two-dimensional, three-dimensional, or four-dimensional (including e.g., time based or velocity based information) images and associated image data sets for reproducing the images.

In some embodiments, the display 110 may display a virtual navigational image in which the actual location of the medical instrument 104 is registered (i.e., dynamically referenced) with preoperative or concurrent images to present the clinician or surgeon S with a virtual image of the internal surgical site from the viewpoint of the location of the tip of the instrument 104. An image of the tip of the instrument 104 or other graphical or alphanumeric indicators may be superimposed on the virtual image to assist the surgeon controlling the medical instrument. Alternatively, the instrument 104 may not be visible in the virtual image.

In other embodiments, the display 110 may display a virtual navigational image in which the actual location of the medical instrument is registered with preoperative or concurrent images to present the clinician or surgeon S with a virtual image of medical instrument within the surgical site from an external viewpoint. An image of a portion of the medical instrument or other graphical or alphanumeric indicators may be superimposed on the virtual image to assist the surgeon controlling the instrument 104.

The teleoperational medical system 100 also includes a control system 112. The control system 112 includes at least one memory and at least one processor (not shown), and typically a plurality of processors, for effecting control between the medical instrument system 104, the operator input system 106, the sensor system 108, and the display system 110. The control system 112 also includes programmed instructions (e.g., a computer-readable medium storing the instructions) to implement some or all of the methods described in accordance with aspects disclosed herein. While control system 112 is shown as a single block in the simplified schematic of FIG. 1, the system may include two or more data processing circuits with one portion of the processing optionally being performed on or adjacent the teleoperational assembly 102, another portion of the processing being performed at the operator input system 106, and the like. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 112 supports wireless communication protocols such as Bluetooth, IrDA, HomeRF, IEEE 802.11, DECT, and Wireless Telemetry.

In some embodiments, control system 112 may include one or more servo controllers that receive force and/or torque feedback from the medical instrument system 104. Responsive to the feedback, the servo controllers transmit signals to the operator input system 106. The servo controller(s) may also transmit signals instructing teleoperational assembly 102 to move the medical instrument system(s) 104 which extend into an internal surgical site within the patient body via openings in the body. Any suitable conventional or specialized servo controller may be used. A servo controller may be separate from, or integrated with, teleoperational assembly 102. In some embodiments, the servo controller and teleoperational assembly are provided as part of a teleoperational arm cart positioned adjacent to the patient's body.

The control system 112 may further include a virtual visualization system to provide navigation assistance to the medical instrument system(s) 104. Virtual navigation using the virtual visualization system is based upon reference to an acquired dataset associated with the three dimensional structure of the anatomical passageways. More specifically, the virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, or the like. Software alone or in combination with manual input is used to convert the recorded images into segmented two dimensional or three dimensional composite representation of a partial or an entire anatomical organ or anatomical region. An image data set is associated with the composite representation. The composite representation and the image data set describe the various locations and shapes of the passageways and their connectivity. The images used to generate the composite representation may be recorded preoperatively or intraoperatively during a clinical procedure. In an alternative embodiment, a virtual visualization system may use standard representations (i.e., not patient specific) or hybrids of a standard representation and patient specific data. The composite representation and any virtual images generated by the composite representation may represent the static posture of a deformable anatomic region during one or more phases of motion (e.g., during an inspiration/expiration cycle of a lung).

During a virtual navigation procedure, the sensor system 108 may be used to compute an approximate location of the instrument with respect to the patient anatomy. The location can be used to produce both macro-level tracking images of the patient anatomy and virtual internal images of the patient anatomy. Various systems for using fiber optic sensors to register and display a medical implement together with preoperatively recorded surgical images, such as those from a virtual visualization system, are known. For example U.S. patent application Ser. No. 13/107,562 (filed May 13, 2011) (disclosing "Medical System Providing Dynamic Registration of a Model of an Anatomical Structure for Image-Guided Surgery") which is incorporated by reference herein in its entirety, discloses one such system.

The teleoperational medical system 100 may further include optional operation and support systems (not shown) such as illumination systems, steering control systems, irrigation systems, and/or suction systems. In alternative embodiments, the teleoperational system may include more than one teleoperational assembly and/or more than one operator input system. The exact number of manipulator assemblies will depend on the surgical procedure and the space constraints within the operating room, among other factors. The operator input systems may be collocated, or they may be positioned in separate locations. Multiple operator input systems allow more than one operator to control one or more manipulator assemblies in various combinations.

Figure 2:
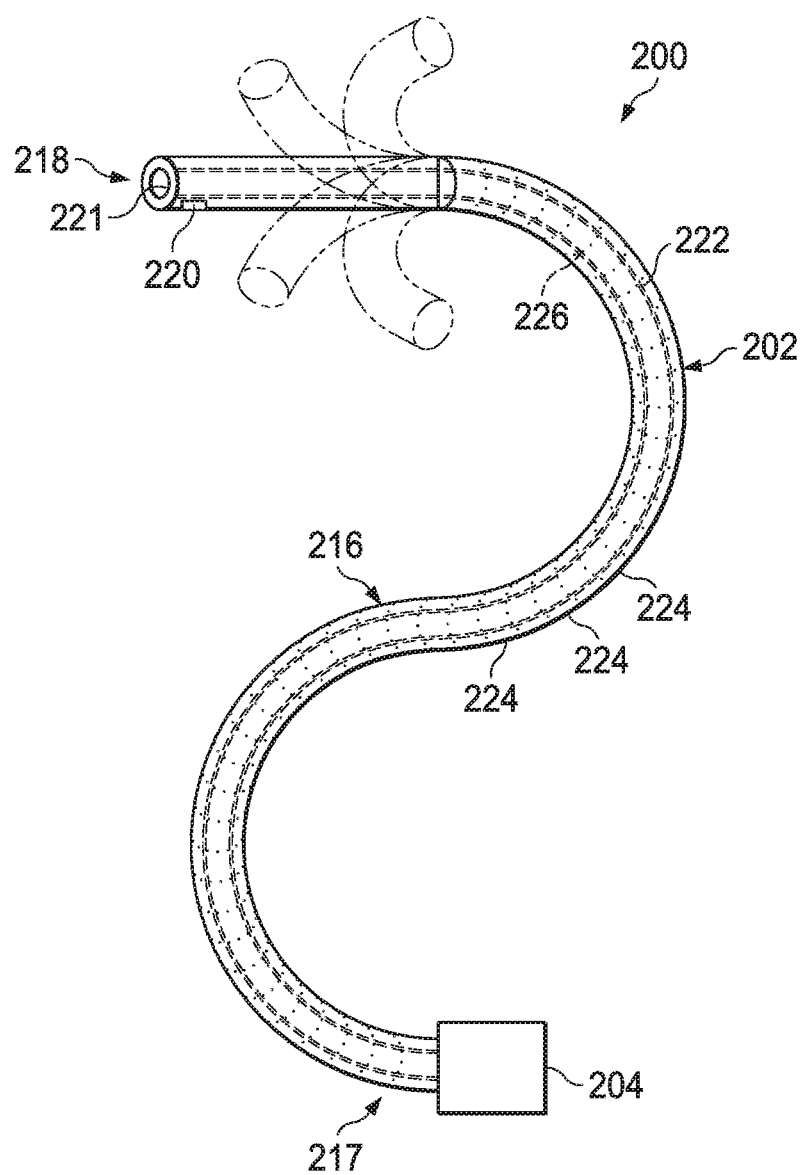
FIG. 2 illustrates an interventional instrument system utilizing aspects of the present disclosure.

FIG. 2 illustrates a medical instrument system 200, which may be used as the medical instrument system 104 of teleoperational medical system 100. Alternatively, the medical instrument system 200 may be used for non-teleoperational exploratory procedures or in procedures involving traditional manually operated medical instruments, such as endoscopy.

The instrument system 200 includes a catheter system 202 coupled to an instrument body 204. The catheter system 202 includes an elongated flexible catheter body 216 having a proximal end 217 and a distal end or tip portion 218. In one embodiment, the flexible body 216 has an approximately 3 mm outer diameter. Other flexible body outer diameters may be larger or smaller. The catheter system 202 may optionally include a shape sensor 222 for determining the position, orientation, speed, velocity, pose, and/or shape of the catheter tip at distal end 218 and/or of one or more segments 224 along the body 216. The entire length of the body 216, between the distal end 218 and the proximal end 217, may be effectively divided into the segments 224. If the instrument system 200 is a medical instrument system 104 of a teleoperational medical system 100, the shape sensor 222 may be a component of the sensor system 108. If the instrument system 200 is manually operated or otherwise used for non-teleoperational procedures, the shape sensor 222 may be coupled to a tracking system 230 that interrogates the shape sensor and processes the received shape data.

The shape sensor 222 may include an optical fiber aligned with the flexible catheter body 216 (e.g., provided within an interior channel (not shown) or mounted externally). In one embodiment, the optical fiber has a diameter of approximately 200 μm. In other embodiments, the dimensions may be larger or smaller. The medical instrument system may optionally include a position sensor system 220. The position sensor system 220 may be a component of an EM sensor system with the sensor 220 including one or more conductive coils that may be subjected to an externally generated electromagnetic field.

The flexible catheter body 216 may include a working channel 221 sized and shaped to receive a medical instrument 226. Interventional instruments may include, for example, image capture probes, biopsy instruments, laser ablation fibers, or other surgical, diagnostic, or therapeutic tools. Interventional tools may include end effectors having a single working member such as a scalpel, a blunt blade, an optical fiber, or an electrode. Other end effectors may include, for example, forceps, graspers, scissors, or clip appliers. Examples of electrically activated end effectors include electrosurgical electrodes, transducers, sensors, and the like. In various embodiments, the interventional tool may be an image capture probe that includes a distal portion with a stereoscopic or monoscopic camera at or near the distal end 218 of the flexible catheter body 216 for capturing images (including video images) that are processed for display. The interventional instrument 226 may house cables, linkages, or other actuation controls (not shown) that extend between the proximal and distal ends of the instrument to controllably bend the distal end of the instrument. Steerable instruments are described in detail in U.S. Pat. No. 7,316,681 (filed on Oct. 4, 2005) (disclosing "Articulated Surgical Instrument for Performing Minimally Invasive Surgery with Enhanced Dexterity and Sensitivity") and U.S. patent application Ser. No. 12/286,644 (filed Sep. 30, 2008) (disclosing "Passive Preload and Capstan Drive for Surgical Instruments"), which are incorporated by reference herein in their entireties.

The flexible catheter body 216 may also houses cables, linkages, or other steering controls (not shown) that extend between the instrument body 204 and the distal end 218 to controllably bend the distal end 218 as shown, for example, by the broken dashed line depictions 219 of the distal end. Steerable catheters are described in detail in U.S. patent application Ser. No. 13/274,208 (filed Oct. 14, 2011) (disclosing "Catheter with Removable Vision Probe"), which is incorporated by reference herein in its entirety. In embodiments in which the instrument system 200 is actuated by a teleoperational assembly, the instrument body 204 may include drive inputs that removably couple to and receive power from motorized drive elements of the teleoperational assembly. In embodiments in which the instrument system 200 is manually operated, the instrument body 204 may include gripping features, manual actuators, or other components for manually controlling the motion of the instrument system. The catheter system may be steerable or, alternatively, the system may be non-steerable with no integrated mechanism for operator control of the instrument bending. Also or alternatively, one or more lumens, through which medical instruments can be deployed and used at a target surgical location, are defined in the walls of the flexible body 216.

In various embodiments, the medical instrument system 200 may include a flexible bronchial instrument, such as a bronchoscope or bronchial catheter, for use in examination, diagnosis, biopsy, or treatment of a lung. The system 200 is also suited for navigation and treatment of other tissues, via natural or surgically created connected passageways, in any of a variety of anatomical systems, including the colon, the intestines, the kidneys, the brain, the heart, the circulatory system, and the like.

In the embodiment of FIG. 2, the instrument 200 is teleoperated within the teleoperational medical system 100. In an alternative embodiment, the teleoperational assembly 102 may be replaced by direct operator control. In the direct operation alternative, various handles and operator interfaces may be included for hand-held operation of the instrument.

When using a teleoperational assembly to insert an instrument catheter into a patient anatomy, the outstretched catheter should be supported as the catheter is advanced into the patient. Otherwise, as the catheter is pushed from a proximal end and encounters friction in the patient anatomy at the distal end, the catheter may buckle or bend. To prevent this deformation of the catheter, an instrument guiding apparatus, as described herein, may be used to provide rigid support to the catheter until it enters the patient anatomy. As the catheter enters the patient anatomy, the guiding apparatus retracts away from the catheter and moves to an unobtrusive location.

Figure 3:
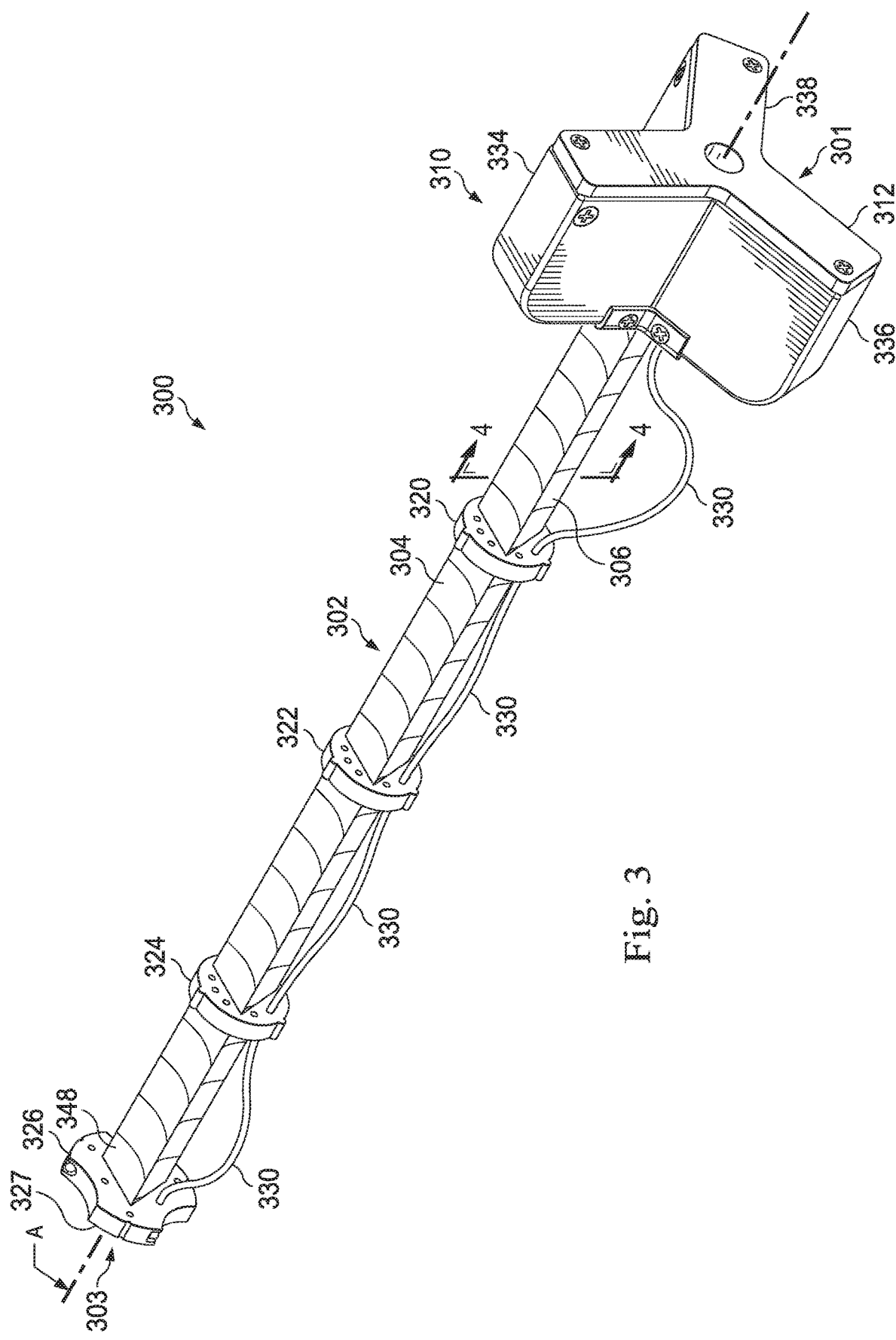
FIG. 3 illustrates an instrument guiding apparatus according to an embodiment of the present disclosure.
Figure 4:
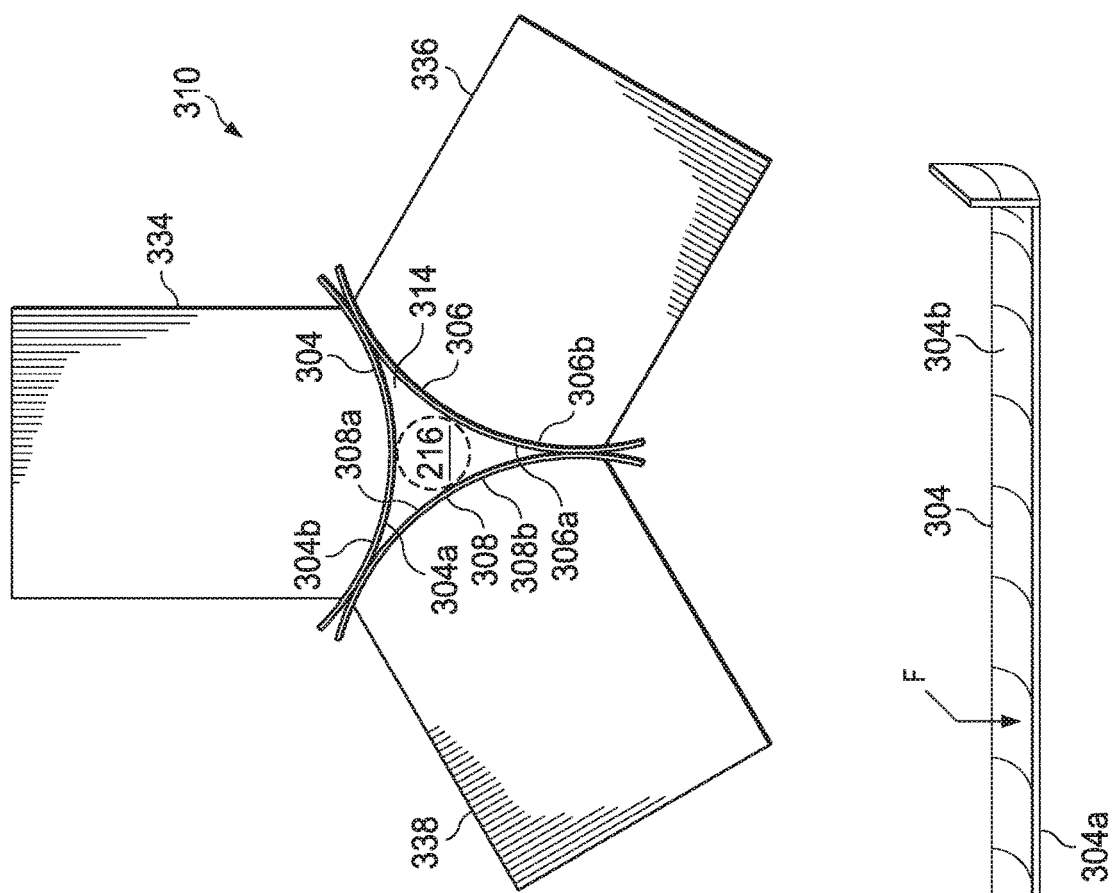
FIG. 4 illustrates a cross-sectional view of the instrument guiding apparatus of FIG. 3.
Figure 5:
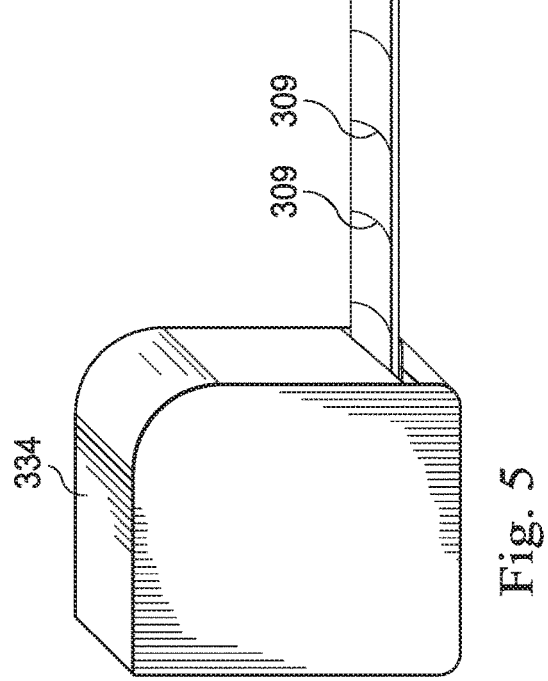
FIG. 5 illustrates a support member and retraction assembly of the embodiment of FIG. 3.

FIG. 3 illustrates an instrument guiding apparatus 300 according to one embodiment of the present disclosure. The instrument guiding apparatus 300 has a distal end 301 and a proximal end 303. The instrument guiding apparatus 300 includes a retractable channel assembly 302 formed from a plurality of support members 304, 306, 308. As shown more clearly in the cross-sectional view of FIG. 4, the support members 304, 306, 308 are arranged to form a generally triangular-shaped channel passageway 314 sized to receive and longitudinally support the instrument catheter body 216. The passageway 314 and the instrument catheter body 216 extend generally along a longitudinal axis A. In this embodiment, the retractable channel assembly 302 is formed from three support members, but in alternative embodiments, fewer or more support members may be used to form a channel passageway. In this embodiment, the support member 304 has an elongated convex surface 304a and an elongated concave surface 304b (See FIG. 5). The support member 306 has an elongated convex surface 306a and an elongated concave surface 306b. The support member 308 has an elongated convex surface 308a and an elongated concave surface 308b. The channel passageway 314 is bounded by the elongated convex surfaces 304a, 306a, 308a. As shown in FIG. 5, the curved profiles of each of the support members 304, 306, 308 allow them to be more resistant to a bending force F than they would be if they were formed with a generally flat profile. The support members may have length markings 309 (e.g., in inch or centimeter intervals) useful for allowing the clinician to gauge the changing length of the retractable channel as it extends or retracts. Thus, the markings 309 are useful to gauge the length of the catheter that has entered or exited the patient anatomy.

Figure 9:
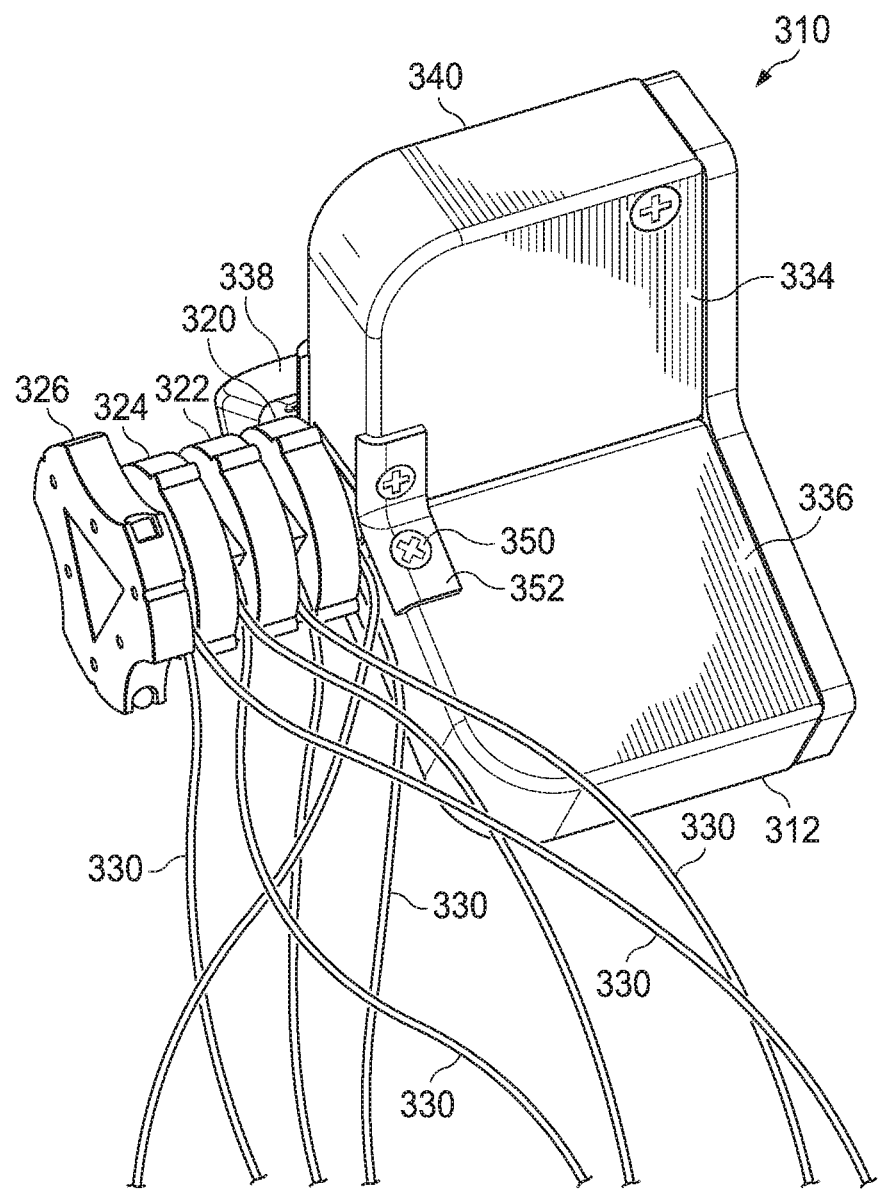
FIG. 9 illustrates the instrument guiding apparatus of FIG. 3 in a retracted configuration.
Figure 10:
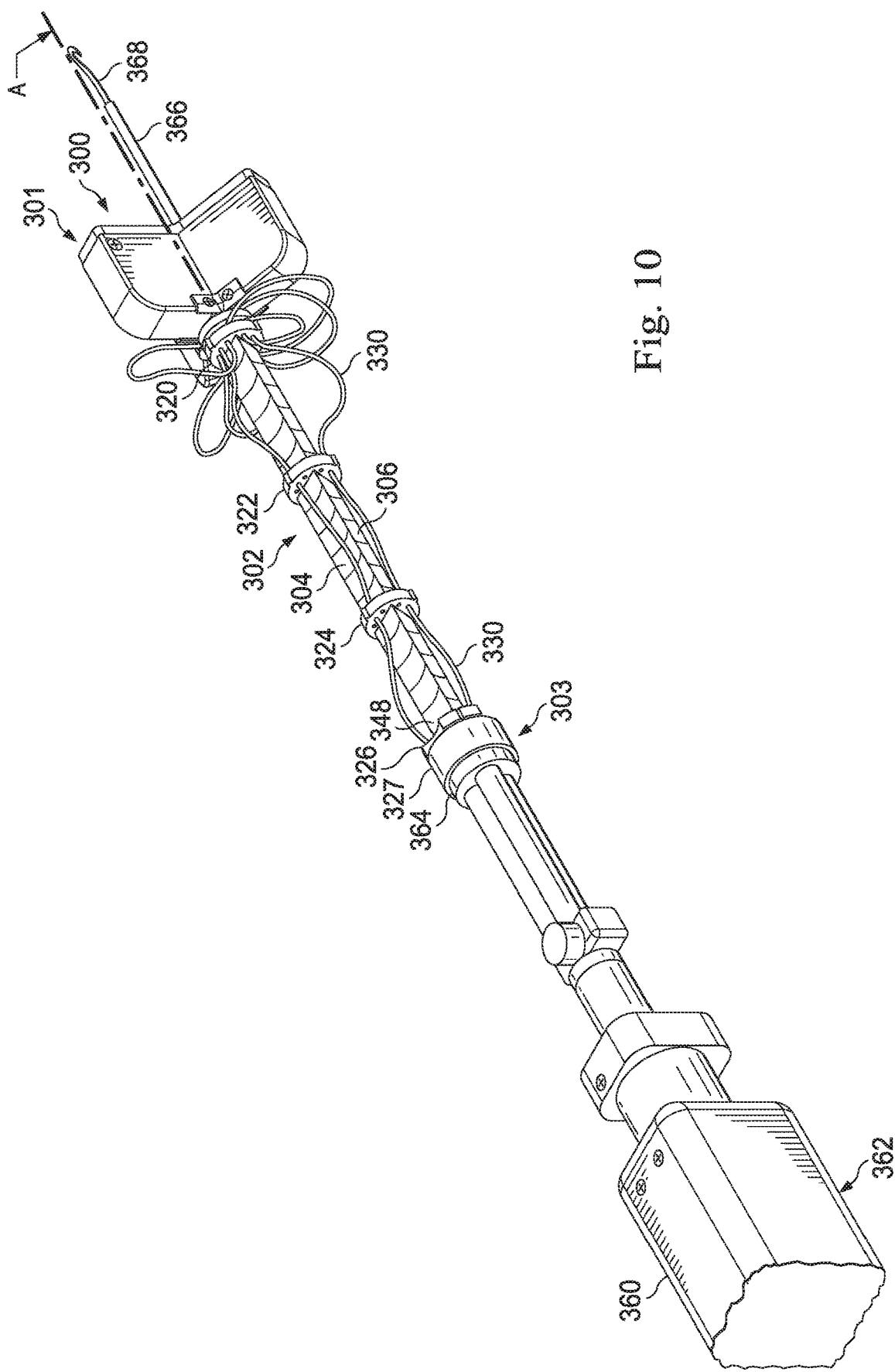
FIG. 10 illustrates the instrument guiding apparatus of FIG. 3 coupled to a medical instrument system.

Referring again to FIG. 3, the instrument guiding apparatus 300 further includes retention members 320, 322, 324, 326 through which the support members 304, 306, 308 extend. The retention members are slidable along the support members. The retention members function to hold the support members in the channel formation and prevent the catheter body 216 from slipping out from between the support members. In this embodiment, the retention members are rings that surround the support members at discrete locations along the longitudinal axis A. The retention members are moved close together (See FIG. 9) when the retractable channel assembly 302 is retracted and become separated by sliding along the support members when the channel assembly is extended. In alternative embodiments, the retention members may be clips, bands, magnets, or other connecting members for holding the support members in the channel formation. More or fewer retention members may be used than are shown in FIG. 3. A terminal retention member 326 couples proximal ends of the support members 304, 306, 308 together to maintain the channel formation. The terminal retention member 326 further including a coupling member 327 sized and shaped to couple with instrument body 204 as shown in FIG. 10. In this embodiment, the retention members 320, 322, 324 and the terminal retention member 326 are coupled in series by tethers 330. Tethers 330 limit the spacing distance between the members 320, 322, 324, 326. For example, in the present embodiment the tethers may limit the spacing between the retention members to approximately 6 inches. Each tether 330 extends between and terminates to adjacent retention members. In alternative embodiments, elongated sheaths or sterile drape sheets may extend between the retention members. These sheaths or sheets may serve as a tether, providing the predetermined spacing between adjacent retention members. In alternative embodiments, the channel formation may be maintained by support members with interlocking, zipper-like teeth.

The instrument guiding apparatus 300 also includes a retraction system 310 including a housing 312 into which the support members 304, 306, 308 may be retracted. In this embodiment, the retraction system 310 includes retraction assemblies 334, 336, 338. The retraction assembly 334 retracts the support member 304. The retraction assembly 336 retracts the support member 306. The retraction assembly 338 retracts the support member 308. With the support members coupled together by the terminal retention member 326, the retraction assemblies 334, 336, 338 may operate generally in unison to retract the support members at the same rate, with approximately equal lengths of each of the support members remaining extended from the retraction assemblies.

Figure 6:
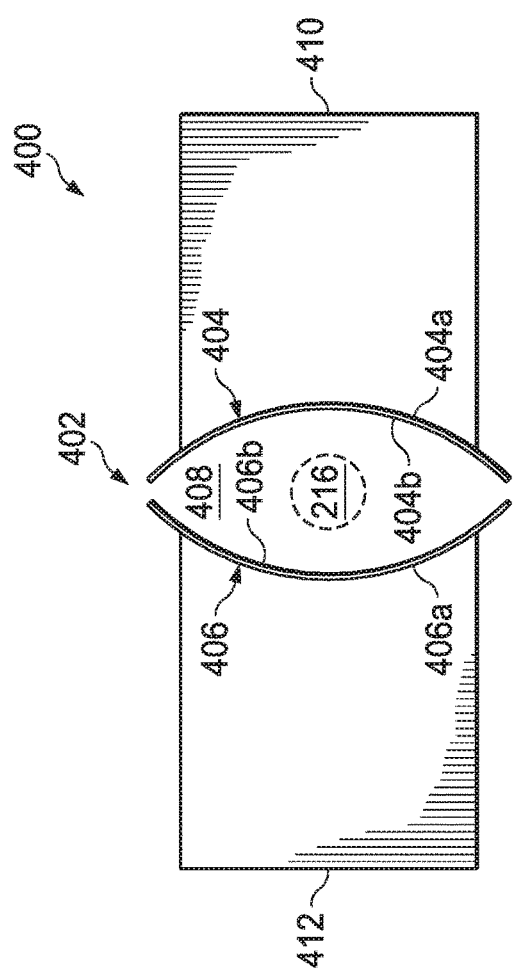
FIG. 6 illustrates a cross-sectional view of an instrument guiding apparatus according to another embodiment of the present disclosure.
Figure 7:
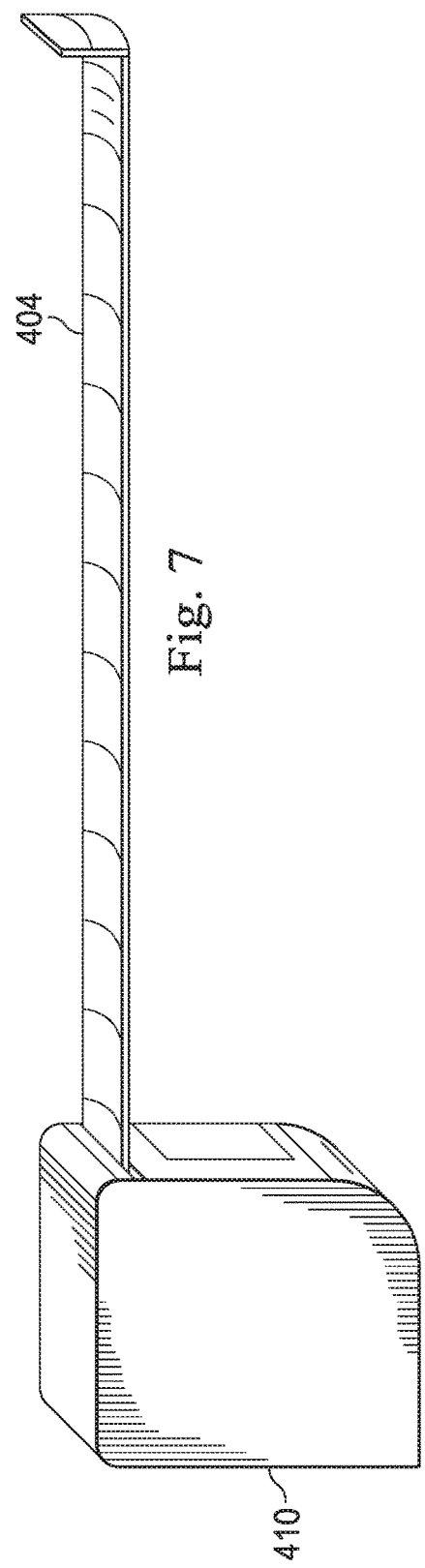
FIG. 7 illustrates a support member and retraction assembly of the embodiment of FIG. 6.

FIG. 6 illustrates a cross-sectional view of an instrument guiding apparatus 400 according to another embodiment of the present disclosure. The instrument guiding apparatus 400 includes a retractable channel assembly 402 formed from two support members 404, 406. The support members 404, 406 are arranged to form a channel passageway 408 having a generally elliptical or almond-shaped cross-sectional shape. The passageway 408 is sized to receive and longitudinally support the instrument catheter body 216. In this embodiment, the support member 404 has an elongated convex surface 404 a and a concave surface 404 b. The support member 406 has an elongated convex surface 406 a and a concave surface 406 b. The channel passageway 408 is bounded by the elongated concave surfaces 404 b, 406 b. The instrument guiding apparatus 400 may further include retention members, as previously described, to hold the support members in the channel formation and prevent the catheter body 216 from slipping between the support members. The instrument guiding apparatus 400 also includes retraction assemblies 410, 412 similar to those described above. The retraction assembly 410 retracts the support member 404. The retraction assembly 412 retracts the support member 406. FIG. 7 illustrates the support member 404 extended from the retraction assembly 410.

Figure 8:
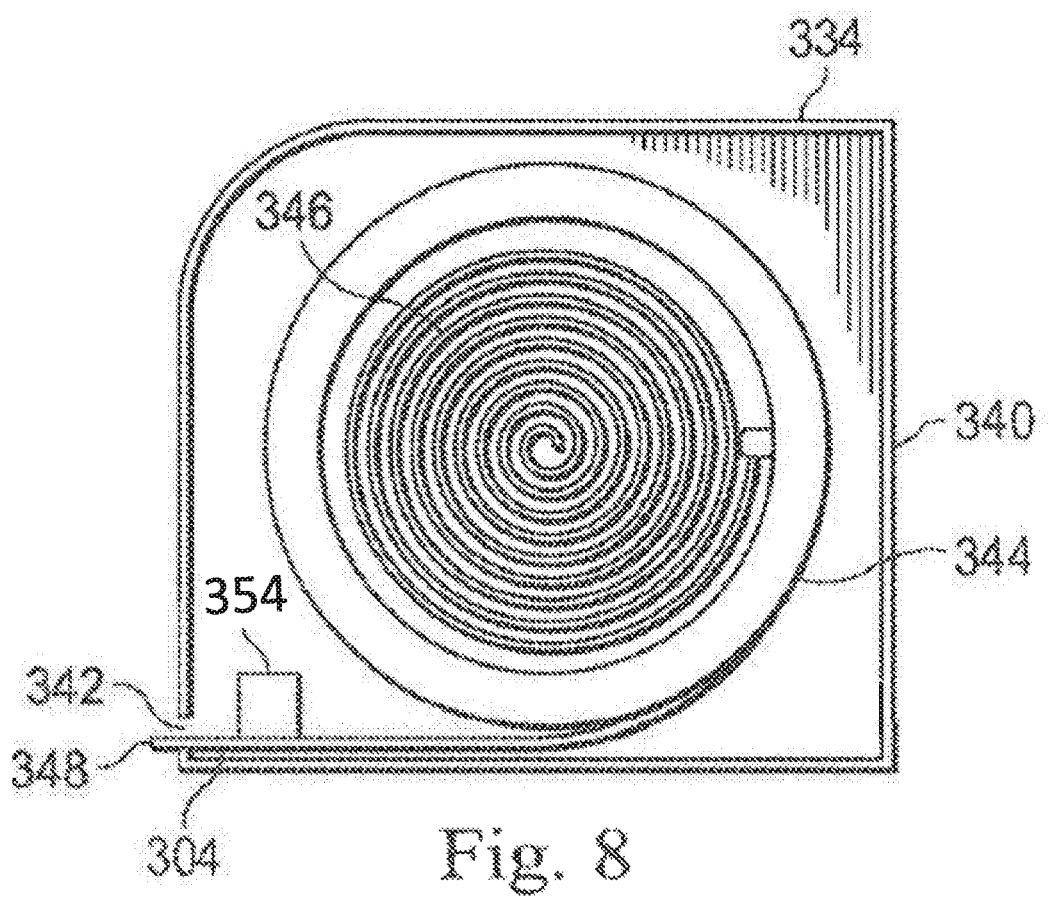
FIG. 8 is a schematic cross-sectional view of a retraction assembly according to an embodiment of the present disclosure.

In the various embodiments described above, each paired retraction assembly and support member may function generally as a retractable tape measure. The support members may be formed from metal, polymeric, fiberglass, or a composite material tape. FIG. 8 provides a schematic cross-sectional illustration of the retraction assembly 334 and support member 304. The retraction assemblies 336, 338, 410, 412 may operate similarly to retraction assembly 334. The support members 306, 308, 404, 406 may operate similarly to support member 304. The retraction assembly 334 includes a housing 340 with an opening 342 through which the support member 304 extends. The opening 342 may be curved to accommodate passage of the curved support member or may have an opening height large enough to accommodate passage of the curvature. Inside the housing 340, the support member 304 is wound around a spool 344, which is rotatably coupled within the housing. The spool 344 is coupled to a coiled return spring 346. The support member 304 has an extended configuration, as shown in FIG. 3 and a collapsed configuration, as shown in FIGS. 8 and 9. In the extended configuration, an end 348 of the support member 304 may be drawn away from the housing 340, causing the support member to overcome the bias of spring 346 and to unwind from the spool 344. In a retracted or collapsed configuration, the return spring 346 biases the spool 344 to return the support member to the wound configuration. A braking mechanism 354 may restrict the rewinding motion to maintain the support member 304 in an extended configuration against the bias of the spring. In alternative embodiments, the spool may be eliminated and the support member may be coupled directly to the return spring.

In various embodiments, the support members are biased toward a straightened, extended configuration. The bias of the return spring may be greater than, less than, or approximately equal to the bias of the support member. If the return spring has a greater bias than the support member, the support member will tend to retract into the housing. A braking mechanism may be used to keep the support member extended. If the support member has a greater bias than the return spring, the support member will tend toward an extended configuration. An external force may be used to retract the support member into the housing. If the support member and the return spring biases are approximately equal, the support member will tend to be in equilibrium at any extended length. Equal biases may result in the lowest operating force.

In another alternative embodiment, the spring may be eliminated and the support member may be returned to a retracted configuration by applying a longitudinal force to the end 348 to rewind the support member. Other spring mechanisms, braking mechanisms, housing configurations, and features associated with conventional retractable tape measure devices may also be suitable for use. Lubricants or other friction-reducing materials may be used to reduce the force needed collapse the channel assembly 302. In alternative embodiments, the support members may retract by collapsing into a zig-zag stack, a cylindrical coil, or other low-profile collapsed configuration within the retraction assembly.

FIG. 9 illustrates the retraction system 310 with the support members 304, 306, 308 in a collapsed or retracted configuration. The support members 304, 306, 308, coupled by the terminal retention member 326, retract in unison so that for any length of the channel passageway 314, the lengths of the support members extended from the housing 312 are approximately equal. In the fully retracted configuration of FIG. 9, the retention members 320, 322, 324, 326 are drawn together. In this embodiment, the housings (including housing 340) that house the individual retraction assemblies 334, 336, 338 form the housing 312. Coupling members 350 and brackets 352 couple the retraction assemblies 334, 336, 338 together. In alternative embodiments, functions of the retraction assemblies may be combined. For example a common spring mechanism may be used to control the retraction of all of the support members. In an alternative embodiment the housing 312 may be a common casing that encloses individual retraction assemblies 334, 336, 338.

FIG. 10 illustrates the instrument guiding apparatus 300 coupled to an instrument body 360 (e.g., instrument body 204) that includes a manipulator interface portion 362. The instrument body 360 also includes a coupling member 364. A catheter system 366 (e.g., catheter system 202) is coupled to the instrument body 360. An instrument 368 extends through the catheter 366. The manipulator interface portion 362 includes drive inputs to provide mechanical coupling of the catheter steering mechanism and/or the instrument 368 to the drive motors mounted to the manipulator assembly. For example, a pair of drive inputs may control the pitch motion of the distal end of the flexible body of the catheter 366, with one adaptor of the pair controlling motion in the upward direction and the other of the pair controlling motion in the opposite downward direction. Other pairs of drive inputs may provide opposing motion in other degrees of freedom for the flexible body and/or the end effector. Instrument interfacing with teleoperational manipulators is described, for example in U.S. Pat. No. 6,331,181, filed Oct. 15, 1999, disclosing "Surgical Robotic Tools, Data Architecture, And Use" and U.S. Pat. No. 6,491,701, filed Jan. 12, 2001 disclosing "Mechanical Actuator Interface System For Robotic Surgical Tools" which are both incorporated by reference herein in their entirety. The manipulator interface portion 362 may also control instrument insertion by moving linearly along the longitudinal insertion axis A.

As shown in FIG. 10, to couple the instrument guiding apparatus 300 to the instrument body 360, the support members 304, 306, 308 may be drawn from the housing 312 to form a channel passageway 314 sufficiently long to support a length of the catheter 366. For example, the support members may extend to approximately three feet. The catheter 366 is inserted into the proximal end 303 of the instrument guiding apparatus 300 with the distal end of the catheter portion exiting from the distal end 301 of the instrument guiding apparatus. The coupling 327 rigidly couples the retractable channel assembly 302 to the instrument body 360 at the coupling member 364, for example via a spring-loaded clamp connection, a threaded coupling, set screws, or any other type of connector.

Figure 11:
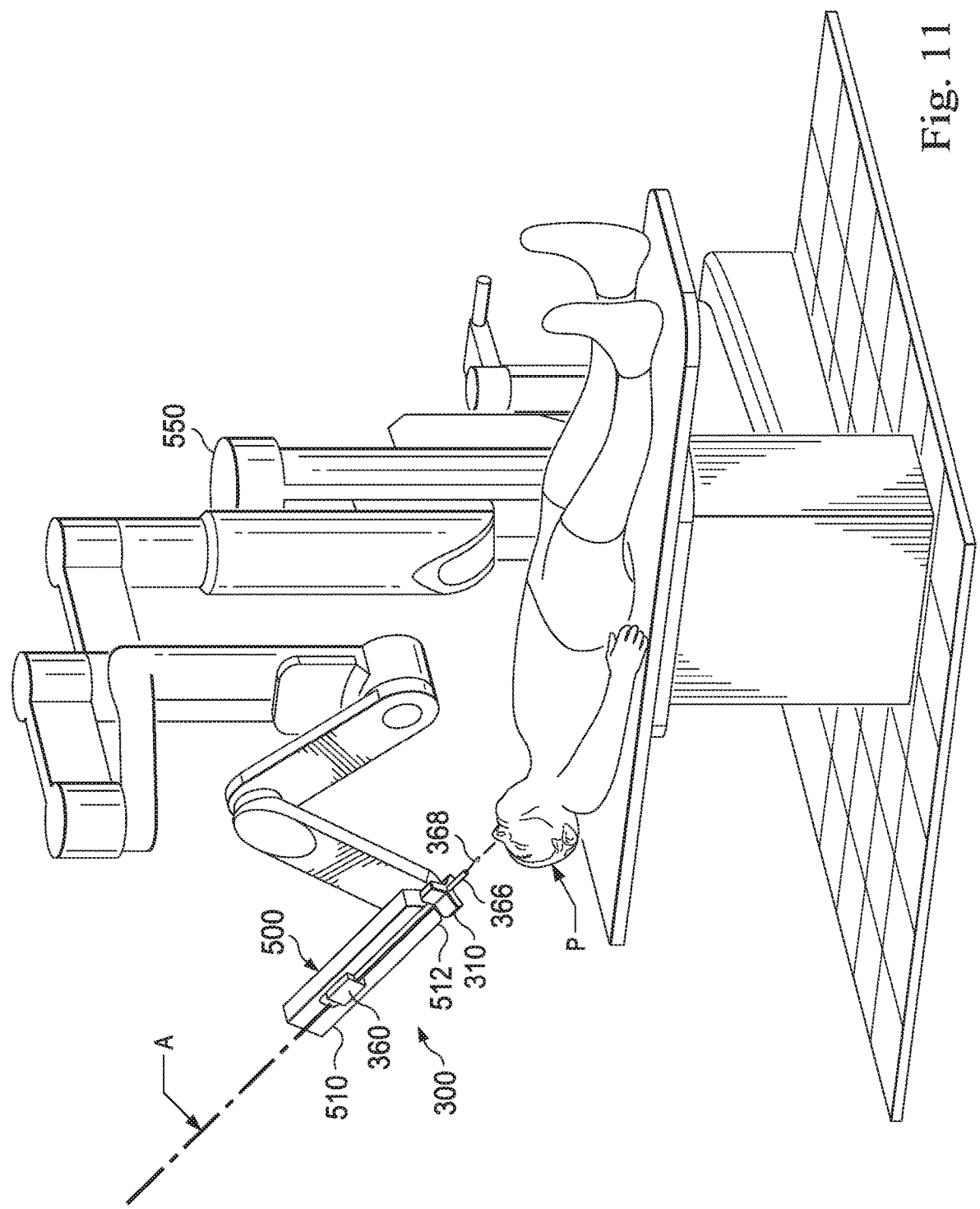
FIG. 11 illustrates the interventional instrument and instrument guiding apparatus of FIG. 10 coupled to a teleoperational assembly in a patient environment according to an embodiment of the present invention.

FIG. 11 illustrates the instrument body 360 and instrument guiding apparatus 300 coupled to an arm 500 of teleoperational manipulator assembly 550 and positioned in a surgical environment with a patient anatomy P. The arm 500 has a proximal end 510 and a distal end 512. The instrument body 360 is movable with respect to the arm 500 along the insertion axis A. The retraction system 310 is coupled to the distal end 512 of the arm 500. Fixing the retraction system 310 at the distal end of the arm 500 prevents or limits the catheter from slipping between support members and limits the mass that must be carried by the moving carriage assembly to which the instrument body is attached. With the instrument guiding apparatus 300 coupled to the instrument body 360, the channel passageway 314 and the support members 304, 306, 308 are in a collapsed or retracted configuration when the instrument body is moved near the distal end 512 of the arm 500. As the instrument body moves along the axis A toward the proximal end 510 of the arm 500, the channel passageway 314 and the support members 304, 306, 308 extend into an extended configuration. The maximum extended configuration of the channel passageway 314 may be determined by the proximal-most position of the instrument body 360. The elongated flexible catheter 366 extends generally along the insertion axis A when the instrument body 360 is coupled via the interface portion 362 to the manipulator assembly arm 500. To support the longitudinal length of the catheter 366 during insertion into the patient anatomy P, a clinician inserts the catheter into the channel passageway 314 and extends the retractable channel assembly 302 to support the entire length of the catheter or at least a sufficiently substantial portion of the catheter to prevent sagging, buckling, or other deformation of the catheter. As the support members 304, 306, 308 are extended, the retention members 320, 322, 324, 326 become separated until further separation is limited by the tethers 330. At maximum separation, the retention members may be, for example, approximately 6 inches apart. Shorter or longer spacing between retention members may also be suitable. The instrument 368 may be inserted into the catheter 366 when the support members are in their retracted configuration, their extended configuration, or at any stage in between.

As the instrument body 360 is advanced, under a clinician's control, distally along the insertion axis A, it also moves the catheter 366 and the proximal end 303 of the instrument guiding apparatus 300 distally. While the catheter is moving distally along the axis A, at the distal end 301 of the instrument guiding apparatus 300, the support members separate and are retracted into the retraction system 310. The retraction of the support members occurs generally in unison such that the remaining extended, unretracted lengths of the support members are generally equal in length. The springs in the retraction system 310 may be selected to counteract the weight of the instrument body and channel, thus providing a controlled retraction of the support members. As the support members are wound into the retraction assembly, the catheter 366 continues to advance distally past the distal end 301 of the instrument guiding apparatus 300 for insertion into the patient anatomy P. Thus, the channel assembly 302 supports the length of the catheter 366 remaining outside of the patient anatomy P, but collapses to minimize cumbersome support structure as the catheter is inserted into the patient. As the catheter is removed from the patient anatomy P, the support members 304, 306, 308 again become extended, reassembling into the retractable channel assembly 302 to support the withdrawn catheter.

The retractable channel assembly 302 may support the catheter 366 along its complete or partial length. The channel assembly 302 alone or in combination with the retention members may be generally resistant to forces perpendicular to the insertion axis A. and thus the retractable channel assembly 302 minimizes bending or buckling of the catheter 366 as the distal end of the catheter is advanced into the patient anatomy P. Any significant bending or buckling of the catheter 366 may damage optical fibers used for shape sensing or endoscopy. Also, bending or buckling may make advancing the catheter non-intuitive, since the user will observe no distal tip movement even though the user is advancing the proximal end of the catheter.

Figure 12:
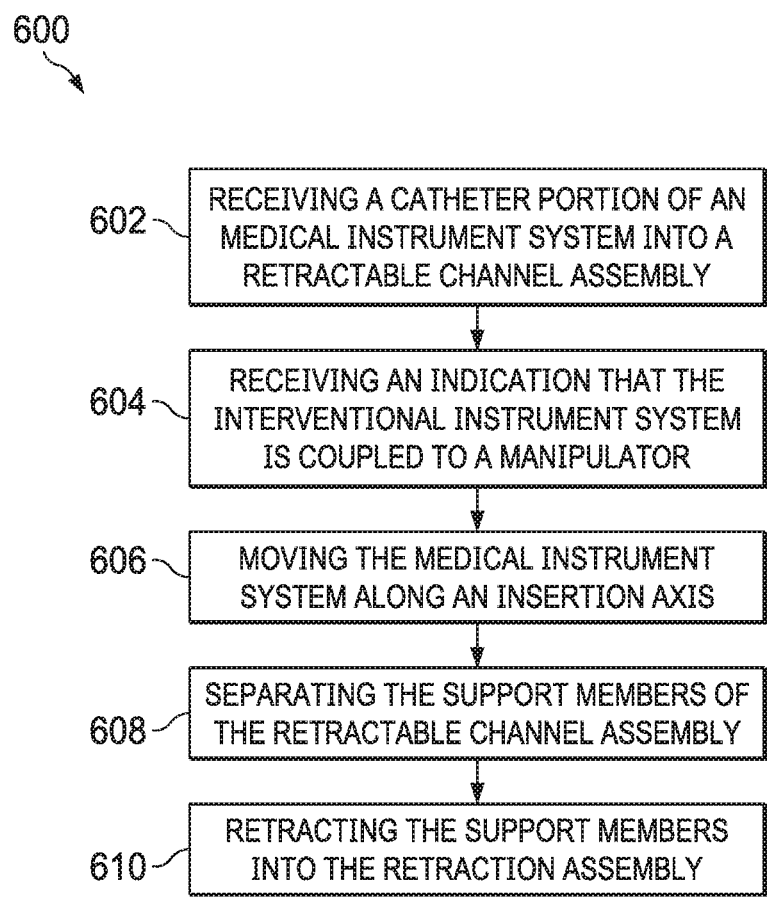
FIG. 12 is a flowchart describing a method of guiding an interventional instrument according to an embodiment of the present disclosure.

FIG. 12 provides a method 600 of guiding a medical instrument (e.g., instrument 368) using the instrument guiding apparatus 300. At 602, the method 600 includes receiving a catheter portion of a medical instrument system into a support assembly, such as the instrument guiding apparatus. At 604, the method 600 includes receiving an indication at the teleoperational control system that the medical instrument system is coupled to the teleoperational manipulator. At 606, the method 600 includes advancing the medical instrument system along the insertion axis A. At 608, the method 600 includes separating the distal end of channel assembly into separated support members. As the channel assembly is incrementally separated, the distal catheter portion of the interventional instrument is advanced distally into the patient anatomy. The proximal portion of the catheter remains supported by the channel assembly. The location at which the support assembly is separated may be located as close as is practicable to the entrance to the patient anatomy to limit the length of the catheter that is unsupported between the support assembly and the entrance to the patient anatomy. At 610, the method 600 includes retracting the separated support members into their respective retraction assemblies Although the systems and methods of this disclosure have been described for use in the connected bronchial passageways of the lung, they are also suited for navigation and treatment of other tissues, via natural or surgically created connected passageways, in any of a variety of anatomical systems including the colon, the intestines, the kidneys, the brain, the heart, the circulatory system, or the like. The methods and embodiments of this disclosure are also suitable for non-interventional applications.

One or more elements in embodiments of the invention may be implemented in software to execute on a processor of a computer system such as control system 112. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet, intranet, etc.

Note that the processes and displays presented may not inherently be related to any particular computer or other apparatus. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A guiding apparatus comprising:
a plurality of support members, wherein each of the plurality of support members has a curved profile to resist bending in at least one direction; and
a retraction system coupled to the plurality of support members,
wherein the plurality of support members has an extended configuration in which the plurality of support members is positioned in an arrangement to form a channel sized to receive an instrument, and
wherein the plurality of support members has a retracted configuration in which each of the plurality of support members is retracted within the retraction system as the instrument is advanced along a longitudinal axis.

2. The guiding apparatus of claim 1, wherein the retraction system comprises a plurality of retraction assemblies, wherein each of the plurality of retraction assemblies is coupled to a corresponding one of the plurality of support members, and wherein the plurality of retraction assemblies operates in unison to retract a corresponding one of the plurality of support members within the plurality of retraction assemblies.

3. The guiding apparatus of claim 1, further comprising a plurality of retaining members coupled to the plurality of support members, wherein the plurality of retaining members are configured to retain the plurality of support members in the arrangement to form the channel.

4. The guiding apparatus of claim 3, wherein each of the plurality of retaining members is tethered to another of the plurality of retaining members by one of a cable, a flexible sheath, or a drape.

5. The guiding apparatus of claim 1, wherein each of the plurality of support members include interlocking features configured to interlock with complementary interlocking features of adjacent support members of the plurality of the support members to form the channel.

6. The guiding apparatus of claim 1, wherein the channel has a cross-sectional shape that is triangular or elliptical.

7. The guiding apparatus of claim 1, wherein the plurality of support members includes three support members.

8. The guiding apparatus of claim 1, wherein each of the plurality of support members includes a convex inner face positioned to at least partially define a perimeter of the channel, and wherein each of the plurality of support members includes a concave outer face.

9. The guiding apparatus of claim 1, wherein each of the plurality of support members includes a concave inner face positioned to at least partially define a perimeter of the channel, and wherein each of the plurality of support members includes a convex outer face.

10. The guiding apparatus of claim 1, wherein the retraction system includes a housing defining a housing opening configured to accommodate passage of one of the plurality of support members, and wherein the housing opening is shaped complementary to an outer profile of a corresponding one of the plurality of support members.

11. The guiding apparatus of claim 1, wherein the retraction system includes a return spring, and wherein the return spring is configured to bias one of the support members towards a retracted position.

12. A system comprising:
an elongated instrument; and
a guiding apparatus comprising:
a plurality of support members, wherein each of the plurality of support members has a curved profile to resist bending in at least one direction, and wherein the plurality of support members is positioned in an arrangement to form an instrument channel sized to receive the elongated instrument; and
a retraction system coupled to the plurality of support members, wherein the retraction system is configured to retract the plurality of support members as the elongated instrument is advanced along a longitudinal axis.

13. The system of claim 12, wherein the retraction system comprises a plurality of retraction assemblies, wherein each of the plurality of retraction assemblies is coupled to a corresponding one of the plurality of support members, and wherein each of the plurality of retraction assemblies operate in unison to retract a corresponding one of the plurality of support members within the retraction assemblies.

14. The system of claim 12, further comprising a plurality of retaining members coupled to the plurality of support members, wherein the plurality of retaining members are configured to retain the plurality of support members in the arrangement defining the instrument channel.

15. The system of claim 12, wherein each of the plurality of support members include interlocking features configured to interlock with complementary interlocking features of adjacent support members of the plurality of the support members to form the instrument channel.

16. The system of claim 12, wherein each of the plurality of support members includes a convex inner face positioned to at least partially define a perimeter of the instrument channel, and wherein each of the plurality of support members includes a concave outer face.

17. The guiding apparatus of claim 12, wherein each of the plurality of support members includes a concave inner face positioned to at least partially define a perimeter of the instrument channel, and wherein each of the plurality of support members includes a convex outer face.

18. The system of claim 12, wherein the retraction system includes a housing defining a housing opening configured to accommodate passage of one of the plurality of support members, and wherein the housing opening is shaped complementary to an outer profile of a corresponding one of the plurality of support members.

19. The system of claim 12, wherein the retraction system includes a return spring, and wherein the return spring is configured to bias one of the support members towards a retracted position.

20. The system of claim 12, wherein the elongated instrument is configured to couple with a teleoperational manipulator, and wherein the teleoperational manipulator is configured to cause the elongated instrument to advance along the longitudinal axis.

* * * * *